United States Patent
Ma et al.

(10) Patent No.: US 9,303,217 B2
(45) Date of Patent: Apr. 5, 2016

(54) PROCESSES FOR CATALYTICALLY REFORMING NAPHTHA

(75) Inventors: Aizeng Ma, Beijing (CN); Jieguang Wang, Beijing (CN); Jincheng Pan, Beijing (CN)

(73) Assignees: China Petroleum & Chemical Corporation, Beijing (CN); China Research Institute of Petroleum Processing, Sinopec, Beijing (CN)

( * ) Notice: Subject to any disclaimer, the term of this patent is extended or adjusted under 35 U.S.C. 154(b) by 74 days.

(21) Appl. No.: 13/480,837

(22) Filed: May 25, 2012

(65) Prior Publication Data
US 2013/0020233 A1    Jan. 24, 2013

(30) Foreign Application Priority Data

May 27, 2011  (CN) ............................ 2011 1 0139265
May 27, 2011  (CN) ............................ 2011 1 0139274

(51) Int. Cl.
*C10G 35/085* (2006.01)
*C10G 35/04* (2006.01)
*C10G 35/06* (2006.01)
(Continued)

(52) U.S. Cl.
CPC . *C10G 61/02* (2013.01); *C07C 4/04* (2013.01); *C10G 9/36* (2013.01); *C10G 21/16* (2013.01); *C10G 21/20* (2013.01); *C10G 21/22* (2013.01); *C10G 35/04* (2013.01); *C10G 61/04* (2013.01); *C10G 61/06* (2013.01); *C10G 63/04* (2013.01); *C10G 2300/1044* (2013.01);
(Continued)

(58) Field of Classification Search
CPC ............ C07C 11/04; C07C 2529/00–2529/08; C10G 2300/1044; C10G 35/04; C10G 61/02–61/06; C10G 63/04

USPC ................................ 208/49, 62, 66, 134, 141
See application file for complete search history.

(56) References Cited

U.S. PATENT DOCUMENTS 2,479,110 A * 8/1949 Haensel ......................... 208/139
3,001,927 A * 9/1961 Broughton et al. ............. 208/64
(Continued)

FOREIGN PATENT DOCUMENTS

CN         198610015         7/1987
CN         1095749          11/1994
(Continued)

OTHER PUBLICATIONS

Satterfield, et al, Liquid Sorption Equilibria of Selected Binary Paraffin Systems in NaY zeolite, AIChE Journal, 1973, vol. 20, No. 3, p. 618-619.*

(Continued)

*Primary Examiner* — Renee E Robinson
*Assistant Examiner* — Derek Mueller
(74) *Attorney, Agent, or Firm* — Finnegan, Henderson, Farabow, Garrett & Dunner, LLP

(57) ABSTRACT

Disclosed herein is a process for catalytically reforming naphtha, comprising, in the presence of hydrogen gas, contacting naphtha with at least one reforming catalyst under the conditions of a pressure ranging from 0.15 to 3.0 MPa, a temperature ranging from 300 to 540° C., a volume space velocity ranging from 2.1 to 50 $h^{-1}$, to carry out a shallow catalytic reforming reaction so as to achieve a naphthene conversion ratio of greater than 85 mass %, and a conversion ratio of paraffins to arenes and $C4^-$ hydrocarbons of less than 30 mass %.

17 Claims, 1 Drawing Sheet

(51) Int. Cl.

| | | |
|---|---|---|
| *C10G 61/02* | (2006.01) | |
| *C10G 63/04* | (2006.01) | |
| *C07C 4/04* | (2006.01) | |
| *C10G 21/16* | (2006.01) | |
| *C10G 21/20* | (2006.01) | |
| *C10G 21/22* | (2006.01) | |
| *C10G 61/04* | (2006.01) | |
| *C10G 61/06* | (2006.01) | |
| *C10G 9/36* | (2006.01) | |

(52) U.S. Cl.
CPC ..... *C10G 2300/202* (2013.01); *C10G 2400/02* (2013.01); *C10G 2400/20* (2013.01); *C10G 2400/30* (2013.01)

(56) References Cited

U.S. PATENT DOCUMENTS

| | | | | |
|---|---|---|---|---|
| 3,827,969 | A | * | 8/1974 | Wilson et al. ............ 208/89 |
| 4,950,385 | A | * | 8/1990 | Sivasanker ............ C10G 59/02 208/137 |
| 5,885,439 | A | | 3/1999 | Glover |
| 6,407,301 | B1 | | 6/2002 | Foley et al. |
| 6,652,737 | B2 | * | 11/2003 | Touvelle et al. ............ 208/137 |
| 7,563,358 | B2 | * | 7/2009 | Stavens et al. ............ 208/138 |
| 2006/0205988 | A1 | | 9/2006 | Rice et al. |

FOREIGN PATENT DOCUMENTS

| | | |
|---|---|---|
| CN | 1169337 | 1/1998 |
| CN | 1267708 | 9/2000 |
| CN | 1353005 | 6/2002 |
| CN | 1476474 | 2/2004 |
| CN | 1504404 | 6/2004 |
| CN | 1710030 | 12/2005 |
| CN | 1715368 | 1/2006 |
| CN | 101198574 | 6/2008 |
| CN | 101376823 | 3/2009 |
| GB | 1165972 | 10/1969 |
| GB | 1313367 | 4/1973 |
| TW | 201024400 | 7/2010 |

OTHER PUBLICATIONS

English language abstract of CN 1986100015, Jul. 16, 1987.
English language abstract of CN 1095749, Nov. 30, 1994.
English language abstract of CN 1169337, Jan. 7, 1998.
English language abstract of CN 1353005, Jun. 12, 2002.
English language abstract of CN 1710030, Dec. 21, 2005.

* cited by examiner

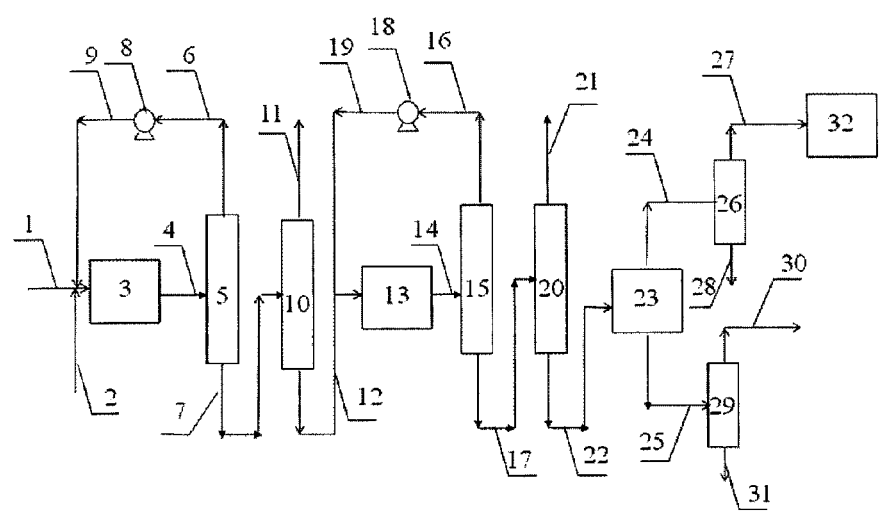

PROCESSES FOR CATALYTICALLY REFORMING NAPHTHA

The present application claims priority to Chinese Patent Application Nos. 201110139274.5 and 201110139265.6, both filed on May 27, 2011.

The present application relates to a process for catalytically reforming naphtha, specifically a catalytic reforming process for producing aromatic hydrocarbons (arenes) and ethylene cracking materials by using naphtha as a feedstock.

Catalytic reforming and steam cracking are mature industrial technologies in the petrochemical field. A purpose of catalytic reforming is to produce arenes, high octane gasoline and hydrogen; a purpose of steam cracking is to produce ethylene and a relatively small amount of propylene. The feedstock of a catalytic reforming device includes naphtha, which is also the main ingredient in the feedstock of a steam cracking device. In view of the heavier crude oil, decrease of naphtha yield, and continuous increase of the global demand for ethylene and arenes, the issue of competing over the feedstock between the catalytic reforming device and the steam cracking device is becoming increasingly remarkable.

During the catalytic reforming process, several competing reactions may occur at the same time, including dehydrogenation of cyclohexane to arene, dehydrogenation and isomerization of alkylcyclopentane to arene, dehydrogenation and cyclization of paraffin to arene, hydrocracking of paraffin to light hydrocarbon products having a boiling range other than that of gasoline, dealkylation of alkylbenzene and isomerization of paraffin. In order to obtain high octane gasoline blending components or arenes, it is desired not only that naphthenes are dehydrogenated and cyclized to arenes, but also that paraffins are converted in a maximum extent to increase the yield of arenes. Thus, highly selective conversion of paraffins to arenes is always a focus and difficulty for the development of reforming technologies.

In order to convert paraffins to arenes, CN1267708A discloses a catalytic reforming process for producing arene-rich products by using three catalyst zones. The process comprises contacting hydrocarbon feedstocks in a catalyst system comprising at least three continuous catalytic regions, wherein the catalyst system comprises one first double-function catalytic reforming area, one zeolite reforming area containing a catalyst comprising a platinum group metal and a non-acidic zeolite, and one final double-function catalytic reforming area. The combined technical process may have a high processing depth and high arene yield, so that it may be suitable for use together with a mobile-bed reforming device, which can continuously regenerate catalysts.

GB1165972 discloses a catalytic reforming process for a petroleum hydrocarbon having a boiling range of gasoline or naphtha, comprising converting a petroleum hydrocarbon containing at least 15% by vol. of naphthenes and at least 25% by vol. of paraffins to a reformate having a research octane number of at least 90 and a hydrogen-containing recycle gas in a plurality of adiabatic fixed-bed reaction zones, at least one naphthene dehydrogenation zone being provided at the front of the plurality of reaction zones, and at least one paraffin dehydrocyclization zone being provided at the back of the plurality of reaction zones; and in the presence of hydrogen and a supported reforming catalyst comprising a Pt-group metal, the catalyst volume ratio of the naphthene dehydrogenation zone to the paraffin dehydrocyclization zone being in the range from 1:20 to 3:1; the hydrogen/oil molar ratio being from 0.5 to 8.0; the first reactor having an inlet temperature maintained at 438-493° C. for at least 80% of the total reforming process time to provide a conversion rate of naphthenes to arenes from 75% to 95% and to form an effluent from the naphthene dehydrogenation zone containing less than 10% by wt. of naphthenes; passing the effluent from the naphthene dehydrogenation zone to the paraffin dehydrocyclization zone, wherein the hydrogen/oil molar ratio ranges from 7 to 30, and the inlet temperature ranges from 482° C. to 538° C., so as to be at least 6.7° C. greater than the inlet temperature of the first reactor of the naphthene dehydrogenation zone for at least 50% of the total reforming process time, in order to form the desired reformate and the hydrogen-containing recycle gas.

GB1313367 discloses a method of reforming a hydrocarbon feedstock, comprising reforming a hydrocarbon feedstock containing naphthenes and paraffins to a reformate, passing the hydrocarbon feedstock and hydrogen gas through a naphthene dehydrogenation reactor filled with a catalyst, which is free of rhenium and comprises a platinum group metal on an alumina support to effect dehydrogenation of naphthenes to form arenes; then passing the hydrocarbon feedstock and hydrogen gas through a naphthene dehydrogenation reactor filled with a catalyst comprising a platinum group metal and rhenium on an alumina support to effect dehydrocyclization of paraffins to form arenes.

Current catalytic reforming technologies primarily focus on how to maximally convert naphthenes and paraffins in naphtha to arenes, rather than on maximally providing the ethylene device with high quality paraffins as the ethylene cracking feedstock when converting naphtha to arenes by reforming.

Naphtha is a mixture comprising many hydrocarbons, such as normal paraffins, isomeric paraffins, naphthenes and arenes. As compared with isomeric paraffins and naphthenes, normal paraffins have a higher yield of ethylene produced by cracking. Benzene rings of arenes are relatively difficult to be cracked under typical cracking conditions and contribute little to the production of ethylene. However, naphthenes are easy to be converted to arenes under catalytic reforming conditions and are catalytic reforming feedstock of good quality. Thus, there is a need to optimize the feedstocks used in the catalytic reforming and steam cracking devices.

Rectification is an effective method for separating naphtha to narrow fractions, but it is difficult to separate normal paraffins from other hydrocarbons.

The adsorption separation technology can separate normal paraffins from naphtha. CN1476474A discloses a method for producing ethylene by steam cracking of normal paraffins, which is a method for preparing a feedstock stream fed into the naphtha reforming device and the stream cracking device. Such method comprises firstly fractionating naphtha into a $C_5$ paraffin stream and $C_6$-$C_9$ hydrocarbon stream, adsorption separating the $C_6$-$C_9$ hydrocarbon stream, selectively adsorbing normal alkanes, using the $C_5$ paraffin stream obtained by fractionation as a desorbent, feeding the normal alkanes separated from $C_5$ paraffins in the desorption solution into a steam cracking zone for producing ethylene, and feeding the raffinate oil into a reforming zone for producing high octane gasoline.

CN101198574A discloses a method for producing ethylene by steam cracking of normal paraffins, comprising adsorption separating $C_5$-$C_9$ hydrocarbons, separating normal alkanes from non-normal alkanes, using as a desorbent $C_{10}$-$C_{16}$ hydrocarbons and mixtures thereof, feeding the adsorption separated normal paraffins into a steam cracking zone for producing ethylene, and feeding non-normal hydrocarbons into a reforming zone and converting to arenes.

CN1710030A discloses a method for optimized utilization of naphtha, comprising adsorption separating naphtha with 5

A molecular sieves, obtaining a desorbed oil product rich in normal hydrocarbons and a raffinate oil product rich in non-normal hydrocarbons, wherein normal hydrocarbons in the desorbed oil are in a content ranging from 80% to 100% by weight. The desorbed oil can be used as a steam cracking material of good quality or cut to narrow fractions by rectification to prepare reagents and high quality solvent oil products, and the raffinate oil can be used as a catalytic reforming feedstock of good quality or clean gasoline blending component with a high octane number.

Although, upon adsorption separation of naphtha, using normal paraffins as the feedstock for steam cracking can increase the ethylene yield, the demand for naphtha is greatly increased to achieve the same ethylene output since naphtha has a low content of normal paraffins.

Disclosed herein is a process for catalytically reforming naphtha, which produces arenes and simultaneously maximally produces paraffins of good quality from naphtha by a shallow catalytic reforming method. Also disclosed herein is a process for producing arenes and ethylene by using naphtha as a feedstock.

The process for catalytically reforming naphtha disclosed herein comprises, in the presence of hydrogen gas, contacting naphtha with a reforming catalyst under the conditions of a pressure ranging from 0.15 to 3.0 MPa, a temperature ranging from 300 to 540° C. and a volume space velocity ranging from 2.1 to 50 $h^{-1}$, to carry out a shallow catalytic reforming reaction so as to achieve a naphthene conversion ratio of greater than 85 mass %, and a conversion ratio of paraffins to arenes and $C_4^-$ hydrocarbons of less than 30 mass %, wherein $C_4^-$ hydrocarbons are hydrocarbons comprising 4 or less carbon atoms.

The process disclosed herein involves a shallow catalytic reforming method of naphtha, wherein naphthene in naphtha is converted to arenes, and the conversion of paraffins is controlled at the same time, which may obtain paraffins in a maximal amount during the reforming process. Paraffins are a feedstock of good quality for producing ethylene by steam cracking. Thus the process disclosed herein can sufficiently utilize the components in naphtha to convert naphthenes (which are easy to produce arenes) to arenes and to minimize the conversion of paraffins to other substances, so as to maintain more paraffins in the catalytically reformed product. After the separation from arenes in the product, paraffins can be used as a feedstock of good quality in the device for producing ethylene by steam cracking.

DESCRIPTION OF THE DRAWINGS

FIG. 1 shows the schematic diagram of an embodiment of the process disclosed herein.

The present disclosure relates to a shallow catalytically reforming process of naphtha, i.e. controlling the depth of the reforming reaction by controlling the reaction conditions, so as to ensure a substantial conversion of naphthenes in naphtha to arenes and simultaneously avoid the conversion of paraffins as much as possible. The process disclosed herein can minimize paraffin isomerization to branched chain isoalkanes, dehydrocyclization to arenes, hydrogenolysis to methane, and hydrocracking to $C_3$ and $C_4$ alkanes, so as to keep most of the paraffins in the reformed product. Arenes in the reformed product are separated from paraffins, and then paraffins are fed into the steam cracking device to produce ethylene and to obtain propylene and 1,3-butadiene at the same time. These three olefins (ethylene, propylene, and 1,3-butadiene) are called "three olefins" thereafter. By using the same amount of naphtha, the process disclosed herein, as compared with the methods in the art, can produce more light arenes (benzene, toluene, and xylene, which are called "BTX" thereafter), ethylene, propylene and 1,3-butadiene.

The shallow catalytic reforming method disclosed herein involves controlling the depth of the reforming reaction by controlling the reaction conditions, including, for example, the temperature and feedstock space velocity, to minimize the conversion of paraffins. In some embodiments, the naphthene conversion ratio in naphtha is greater than 90 mass %, and the conversion ratio of paraffins to arenes and $C_4^-$ hydrocarbons is less than 10 mass %, wherein $C_4^-$ hydrocarbons are hydrocarbons comprising 4 or less carbon atoms.

In some embodiments, the catalytic reforming reaction in the process disclosed herein may be conducted, for example, at a pressure ranging from 0.2 to 2.0 MPa; a temperature ranging from 350 to 520° C., such as from 400 to 500° C.; a naphtha volume space velocity ranging from 3 to 30 $h^{-1}$, such as from 8.0 to 25.0 $h^{-1}$; and a hydrogen/hydrocarbon volume ratio ranging from 0.1:1 to 20:1, such as from 1:1 to 8:1.

In some embodiments, the catalytic reforming reaction in the process disclosed herein may be conducted by using continuous (mobile-bed) reforming technology, semi-regenerating (fixed-bed) reforming technology, or cyclic regeneration reforming technology.

In one embodiment, the reforming catalyst disclosed herein may comprise from 0.01 to 5.0 mass % of a Group VIII metal, from 0.01 to 5.0 mass % of halogen, and from 90.0 to 99.97 mass % of an inorganic oxide support.

In another embodiment, the reforming catalyst disclosed herein may comprise from 0.01 to 5.0 mass % of a Group VIII metal, from 0.01 to 5.0 mass % of halogen, from 0.01 to 10.0 mass % of a metal chosen from Re, Sn, Ge, Ir and Rh, and from 80.0 to 99.97 mass % of an inorganic oxide support.

In yet another embodiment, the reforming catalyst disclosed herein may further comprise at least one metal constituent chosen from alkaline metals, alkaline earth metals, rare earth elements, In, Co, Ni, Fe, W, Mo, Cr, Bi, Sb, Zn, Cd and Cu.

The inorganic oxide support in the reforming catalyst disclosed herein may be chosen, for example, from alumina, magnesia, chromic oxide, $B_2O_3$, $TiO_2$, $ThO_2$, $ZnO_2$, $ZrO_2$, silica-alumina, silica-magnesia, chromic oxide-alumina, $Al_2O_3$—$B_2O_3$, $SiO_2$—$ZrO_2$, ceramics, aluminas, bauxites, $SiO_2$, silicon carbide, synthetic and natural silicates and clays, crystal silicon-aluminum zeolites, such as X-zeolite, Y-zeolite, mordenite, β-zeolite, Ω-zeolite and L-zeolite, which may be hydrogen-type, such as non-acid type (wherein there may be at least one alkaline metal occupying cation exchangeable positions in the non-acid crystal silicon-aluminum zeolites), and non-silicon-aluminum zeolites, such as phosphoaluminates and phosphoaluminosilicates. In one embodiment, the inorganic oxide support is alumina.

The reforming catalyst disclosed herein may be prepared by a conventional method comprising, for example, firstly preparing a shaped support, which may be spherical or cylinder-shaped, and then impregnating and introducing metal constituents and halogen. If the catalyst disclosed herein comprises the second metal constituent and further comprises the third metal constituent, in some embodiment, the method disclosed herein comprises introducing the second and third metal constituents into the support first, and then introducing the Group VIII metal and halogen. The support into which the metal constituents are introduced is, for example, dried and calcined at a temperature ranging from 450-650° C. to obtain a reforming catalyst in an oxidation state. The reforming catalyst in an oxidation state go, for example, through halogen adjustment. In one embodiment, the halogen introduced into the catalyst may be chlorine, and the halogen adjustment may be conducted by a water-chlorine activating treatment at a temperature ranging from 370-600° C. Before use, the reforming catalyst in an oxidation state needs, for example, to be reduced in a hydrogen atmosphere at a temperature ranging from 315-650° C., to obtain a reforming catalyst in a reduced state. As for a platinum-rhenium reforming catalyst, a pre-vulcanizing treatment may, for example, be conducted.

The naphtha disclosed herein may comprise a hydrocarbon mixture having an ASTM D-86 initial boiling point ranging from 40-80° C., and a final boiling point ranging from 160-220° C. The hydrocarbon mixture may comprise at least one hydrocarbon chosen from $C_5$-$C_{12}$ hydrocarbons, such as alkanes, naphthenes, arenes and olefins.

The naphtha disclosed herein may, for example, comprise from 30 to 85 mass % of alkanes, from 10 to 50 mass % of naphthenes and from 5 to 30 mass % of arenes.

The naphtha disclosed herein may be chosen, for example, from straight run naphtha, hydrocracked naphtha, coked naphtha, catalytically cracked naphtha and field condensate.

The impurities in naphtha, such as olefins, sulfur, nitrogen, arsenic, oxygen, and chlorine, may have adverse effects on the catalytic reforming device and the reforming catalyst. Thus, in some embodiments, naphtha may be hydrorefined, before the reforming reaction, to hydro-saturate olefins contained therein and remove the impurities such as sulfur, nitrogen, arsenic, oxygen, and chlorine, so as to obtain the hydrorefined naphtha.

The hydrorefining reaction of naphtha is, for example, conducted at a temperature ranging from 260 to 460° C., such as from 280 to 400° C.; a pressure ranging from 1.0 to 8.0 MPa, such as from 1.6 to 4.0 MPa; a feedstock volume space velocity ranging from 1 to 20 $h^{-1}$, such as 2 to 8 $h^{-1}$; and a hydrogen/hydrocarbon volume ratio ranging from 10:1 to 1000:1, such as 50:1 to 600:1, during the reaction.

The hydrorefining catalyst have, for example, the capabilities of hydrosaturating olefins, as well as the capabilities of hydro-desulfurization, denitrification and deoxygenation. The hydrorefining catalyst comprises, for example, from 5 to 49 mass % of a hydrogenation active component, from 0.1 to 1.0 mass % of halogen, and from 50.0 to 94.9 mass % of an inorganic oxide support, wherein the hydrogenation active component comprises, for example, an oxide of at least one metal chosen from Co, Ni, Fe, W, Mo, Cr, Bi, Sb, Zn, Cd, Cu, In and rare earth metals. In one embodiment, the inorganic oxide support is alumina.

The hydrorefining catalyst above may be prepared by a conventional method. For example, CN1169337A discloses firstly shaping aluminum hydroxide, calcining in air or water vapor to obtain a γ-alumina support, then introducing the hydrogenating active components by an impregnating method.

As for the hydrorefined naphtha, the following methods may be further used to remove deleterious impurities. For example, CN1353005A discloses removing chlorine in naphtha by using a dichlorinating agent comprising an active component chosen from calcium hydroxide, calcium hydroxide+calcium carbonate, and sodium carbonate+calcium carbonate. CN86100015A discloses removing sulfur in naphtha by using a suitable desulphurizing agent, e.g. consisting of nickel, diatomite, silicon dioxide and alumina. CN1095749A discloses removing arsenic impurities in naphtha by using a suitable arsenic removing agent, e.g. metallic nickel supported on alumina.

The hydrorefined product of naphtha may be separated to obtain a dry gas and a liquefied gas, wherein the resultant liquid product comprises the refined naphtha comprising sulfur in an amount of less than 0.5 μg/g, nitrogen in an amount of less than 0.5 μg/g, arsenic in an amount of less than 1.0 ng/g, and lead in an amount of less than 10 ng/g.

In one embodiment, the process disclosed herein may further comprise the following step 2) subsequent to the aforesaid shallow catalytic reforming reaction step:

2) feeding the reformed product into a gas-liquid separation device to separate hydrogen, liquefied gas and the reformate.

In another embodiment, the process disclosed herein may further comprise the following step 3):

3) passing the reformate through an arene separation device to separate arenes and paraffins and to obtain a fraction rich in arenes and a fraction rich in paraffins.

In yet another embodiment, the process disclosed herein may further comprise the following step 4):

4) feeding the fraction rich in paraffins into a steam cracking device to produce ethylene by cracking.

The combination of the shallow catalytic reforming reaction with the arene separation and steam cracking technology can maximally produce ethylene while producing arenes by catalytic reforming. As compared with conventional catalytic reforming or adsorption separation processes, the process disclosed herein can produce more BTX (benzene, toluene, and xylene), ethylene, propylene and 1,3-butadiene with the same amount of naphtha under the condition of the same arene yield.

Steps 2)-4) above are described in details below.

Subsequent to the shallow catalytic reforming reaction process disclosed herein, the catalytically reformed product obtained by the process disclosed herein can be fed into the gas-liquid separation device to separate hydrogen gas, liquefied gas and the reformate. The operation method of the gas-liquid separation device may comprise cooling the reformed product, then feeding it into a gas-liquid separation tank, and separating hydrogen-rich gas from the liquid phase, wherein the gas-liquid separation tank has an operation temperature ranging from 0 to 65° C.; then feeding the liquid phase product into a fractionating tower, wherein light hydrocarbons lower than $C_4$ or $C_5$ are separated from the top of the tower, and reformate mixtures of hydrocarbons equal or greater than $C_5$ or $C_6$ (i.e. $C_5^+$ hydrocarbons comprising 5 or more carbon atoms, and $C_6^+$ hydrocarbons comprising 6 or more carbon atoms) are obtained at the bottom of the tower.

Arenes and paraffins in the reformate above can be separated by the arene separation device, wherein the arene separation device may be chosen, for example, from an arene extraction device and an arene adsorption separation device, to obtain a fraction rich in arenes and a fraction rich in paraffins.

When arenes in the reformate are separated by the arene extraction device, the extraction solvent used therein may be chosen, for example, from sulfolane, dimethyl sulfoxide, dimethyl formamide, N-methylpyrrolidone, N-formylmorpholine, triglycol, tetraglycol, pentaglycol, methanol, and acetonitrile.

The arene extraction method may be chosen, for example, from a liquid-liquid extraction process and an extraction-distillation process.

The process for separating arenes by liquid-liquid extraction comprises, for example, contacting the reformate with the extraction solvent in the liquid phase in an extraction tower, to obtain a solvent rich in arene compounds at the bottom of the tower, and a raffinate liquid rich in non-arene compounds at the top of the tower, wherein the raffinate liquid may be purified in a scrubbing tower to remove the residual trace solvent to obtain a hydrocarbon mixture rich in paraffins. The solvent rich in arene compounds is fed into a solvent separation tower, wherein arenes are discharged from the top of a recovery tower, and a lean solvent is discharged from the bottom of the recovery tower, and then recycled to the extraction tower.

The process for separating arenes by extraction-distillation comprises, for example, feeding the reformate into an extraction-distillation tower, contacting with the extraction solvent under the gaseous phase condition, wherein non-arene compounds and a small amount of solvent are discharged from the top of the extraction-distillation tower, and a solvent rich in arenes is discharged from the bottom of the extraction-distillation tower and fed into a solvent separation tower, and separating the arene compounds from the solvent, wherein the resultant lean solvent is recycled to the extraction-distillation tower.

The mixed arenes separated from the arene extraction step may be fed into an arene combination device for producing benzene, toluene and xylene, as well as p-xylene by xylene isomerization and adsorption separation. The arene combination device may comprise at least one unit chosen from arene extraction, $C_8$ arene isomerization, adsorption separation, toluene disproportionation and arene transalkylation, and can be used for producing chemical products, such as benzene, toluene, p-xylene, and m-xylene.

After the separation of arenes from the reformed product disclosed herein, the resultant compounds rich in arenes and the hydrocarbon mixtures rich in paraffins may be both used as feedstocks in subsequent reaction devices, so that the arene purity and the content of arenes in the hydrocarbon mixtures rich in paraffins are not strictly limited. Thus. a procedure, which is more simplified than the conventional arene extraction unit, may be used for the extraction of arene compounds. In such case, the solvent separation tower may have lower number of plates, and the mass ratio of the extraction solvent to the extraction feedstocks may range from 1:1 to 10:1, such as from 1:1 to 5:1.

Arenes in the reformed product disclosed herein can be separated from paraffins by an adsorption separation method. In some embodiments, the reformate is fed into an adsorbent bed layer, wherein arenes in the reformate are adsorbed, and non-arenes are discharged from the adsorbent bed layer. Then a desorbing agent is fed into the adsorbent bed layer to desorb the adsorbent bed layer. During the adsorption separation, the adsorbent used therein may be any porous substances having adsorption capabilities to arenes, such as NaX and NaY zeolites.

The paraffin-rich hydrocarbon mixtures obtained by the above arene separation step are suitably used as the steam cracking feedstock for producing ethylene, wherein the steam cracking may be carried out under the conditions of a pressure ranging from 0.05 to 0.30 MPa, a reactant residence time ranging from 0.01 to 0.6 s, a water/oil mass ratio ranging from 0.3:1 to 1.0:1, and a cracking furnace outlet temperature ranging from 760 to 900° C.

One embodiment of the present disclosure is further elaborated below and in FIG. 1.

In FIG. 1, naphtha from pipeline 1 is mixed with a supplementary hydrogen gas from pipeline 2, and then fed into a pre-hydrogenation reactor 3 together with a recycled hydrogen gas from pipeline 9. The pre-hydrogenated product is fed into a gas-liquid separation tank 5 via pipeline 4. A hydrogen-rich gas separated from the upper part of the gas-liquid separation tank 5 is fed into a circulation compressor 8 via pipeline 6 for recycling, and a stream discharged from the bottom of the gas-liquid separation tank 5 is fed into a rectifying tower 10 via pipeline 7. Upon rectification, a liquefied gas is discharged from the system via pipeline 11 at the upper part of the rectifying tower 10, and the refined naphtha is discharged from the bottom of the rectifying tower 10, mixed with a recycled hydrogen gas from pipeline 19 via pipeline 12, and fed into a reforming reactor 13 for the shallow catalytic reforming process disclosed herein. The reformed product is fed into a reformed product gas-liquid separation tank 15 via pipeline 14, wherein the hydrogen-rich gas separated from the upper part of the gas-liquid separation tank 15 is fed into a circulation compressor 18 via pipeline 16 for recycling, and liquid components discharged from the bottom of the gas-liquid separation tank 15 is fed into a reformed product rectifying tower 20 via pipeline 17. A liquefied gas obtained by rectification is discharged from the system from the upper pipeline 21. The reformate is discharged from the bottom of the rectifying tower 20, and fed via pipeline 22 into an arene separation zone 23, which may be chosen from an extraction device and an adsorption separation device, and extracted (or adsorbed) with a solvent to separate arenes from non-arenes. Paraffin-rich components after separation are fed into a water scrubber 26 via pipeline 24. Upon water scrubbing, the paraffin-rich components are fed via pipeline 27 into a steam cracking zone 32 for producing ethylene by steam cracking. A mixture discharged from the bottom of the water scrubber 26 containing the extraction solvent and water is discharged via pipeline 28 and may be recycled to the arene separation zone 23. The solvent rich in arenes discharged from the arene separation zone 23 is fed into a solvent recovery tower 29 via pipeline 25 for separating arenes from the solvent, wherein the arene stream obtained at the upper part of the solvent recovery tower 29 is discharged via pipeline 30 and may be fed into an arene combination device for separating the arene products such as BTX or for subsequent treatments such as xylene isomerization and p-xylene adsorption separation; the lean solvent obtained at the bottom of the solvent recovery tower 29 is discharged via pipeline 31 and may be recycled to the arene separation zone 23.

The present disclosure is further elaborated by the following examples, but is not limited to these examples.

Example 1

This example involves hydrorefining of naphtha.

In a 20 ml fixed-bed continuous flow reactor, 20 ml of hydrorefining catalyst A (RS-1, produced by Sinopec Catalyst Company, Changling Division) was fed comprising 0.03 mass % of CoO, 2.0 mass % of NiO, 19.0 mass % of $WO_3$, 0.7 mass % of F and 78.27 mass % of $Al_2O_3$. The naphtha having the composition and properties listed in Table 1 was hydrorefined under the conditions of a temperature of 290° C., a hydrogen partial pressure of 1.6 MPa, a hydrogen/hydrocarbon volume ratio of 200:1, and a feedstock volume space velocity of 8.0 $h^{-1}$. The product was fed into a water cooler and separated into gaseous and liquid phases, wherein the two phases were respectively measured and their compositions were analyzed. The composition and properties of the refined naphtha are shown in Table 2.

TABLE 1

| | | |
|---|---|---|
| Specific gravity, g/cm³ | | 0.7252 |
| Distillation range, ° C. | Initial boiling point | 79.8 |
| | 10% | 99.8 |
| | 50% | 112.6 |
| | 90% | 144.4 |
| | Final boiling point | 161.3 |

TABLE 1-continued

| Impurity content | Sulfur, μg/g | 428 |
|---|---|---|
| | Nitrogen, μg/g | 0.9 |
| | Arsenic, ng/g | 3.0 |
| | Lead, ng/g | 2.0 |
| Group composition, mass % | Paraffins | 63.22 |
| | Naphthenes | 22.68 |
| | Arenes | 12.48 |
| | Olefins | 1.62 |

TABLE 2

| Specific gravity, g/cm³ | | 0.7255 |
|---|---|---|
| Distillation range, °C. | Initial boiling point | 80 |
| | 10% | 100 |
| | 50% | 112 |
| | 90% | 144 |
| | Final boiling point | 162 |
| Impurity content | Sulfur, μg/g | <0.5 |
| | Nitrogen, μg/g | <0.5 |
| | Arsenic, ng/g | <1 |
| | Lead, ng/g | <1 |
| Group composition, mass % | Paraffins | 64.72 |
| | Naphthenes | 22.78 |
| | Arenes | 12.50 |
| | Olefins | 0.00 |

According to the results in Table 2, it can be seen that, after hydrorefining, the olefin, sulfur, nitrogen, arsenic and lead contents in naphtha meet the requirements of a feedstock for a catalytically reforming reaction.

Examples 2-3

The refined naphtha in Table 2 was catalytically reformed according to the process disclosed herein. PtSn/γ-Al$_2$O$_3$ catalyst B (GCR-100A, produced by HUNAN JIANCHANG PETROCHEMICAL CO., LTD) comprising 0.35 mass % of Pt, 0.30 mass % of Sn, 1.0 mass % of Cl and the remaining mass % of γ-Al$_2$O$_3$ was used in the catalytically reforming reaction.

In a 100 ml fixed-bed continuous flow reactor, 50 ml of catalyst B was fed. The refined naphtha listed in Table 2 as the catalytically reforming feedstock was reformed under the conditions of a reaction feedstock inlet temperature of 500° C., a reaction pressure of 0.34 MPa, a hydrogen/hydrocarbon molar ratio of 6.7:1, and a feedstock volume space velocity of 20.0 h$^{-1}$ in Example 2 and 8.0 h$^{-1}$ in Example 3. The reformed product was rectified to obtain a C$_5$$^+$ reformate. The reaction results are shown in Table 3.

Example 4

The refined naphtha in Table 2 was catalytically reformed according to the process disclosed herein. PtRe/γ-Al$_2$O$_3$ catalyst C (CB-60 catalyst, produced by SINOPEC CATALYST COMPANY, Changling Division) comprising 0.26 mass % of Pt, 0.26 mass % of Re, 1.0 mass % of Cl and the remaining mass % of γ-Al$_2$O$_3$ was used.

In a 100 ml fixed-bed continuous flow reactor, 50 ml of catalyst C was fed. Before use, catalyst C was pre-vulcanized by adding 0.1 mass % of hydrogen sulfide in a hydrogen stream having a temperature of 425° C., to make the sulfur content in the catalyst to reach 0.06 mass %.

The refined naphtha listed in Table 2 as the catalytically reforming feedstock was reformed under the conditions of a reaction feedstock inlet temperature of 475° C., a reaction pressure of 1.4 MPa, a hydrogen/hydrocarbon molar ratio of 6.7:1, and a feedstock volume space velocity of 20.0 h$^{-1}$. The reformed product was rectified to obtain a C$_5$$^+$ reformate. The reaction results are shown in Table 3.

Example 5

The refined naphtha in Table 2 was catalytically reformed according to the process disclosed herein. Pt/γ-Al$_2$O$_3$ catalyst D (high platinum pellet, produced by SINOPEC CATALYST COMPANY, Changling Division) comprising 0.50 mass % of Pt, 0.8 mass % of Cl, and the remaining mass % of γ-Al$_2$O$_3$ was used.

In a 100 ml fixed-bed continuous flow reactor, 50 ml of catalyst D was fed. The refined naphtha listed in Table 2 as the catalytically reforming feedstock was reformed under the conditions of a reaction feedstock inlet temperature of 475° C., a reaction pressure of 1.4 MPa, a hydrogen/hydrocarbon molar ratio of 6.7:1, and a feedstock volume space velocity of 18.0 h$^{-1}$. The reformed product was rectified to obtain a C$_5$$^+$ reformate. The reaction results are shown in Table 3.

Comparative Example 1

The refined naphtha was catalytically reformed according to the process in Example 2, except that the volume space velocity of the feedstock was 2.0 h$^{-1}$. The results are shown in Table 3.

Comparative Example 2

This comparative example shows the catalytic reforming effect of the resultant raffinate oil after adsorption separation of naphtha.

The naphtha listed in Table 1 was fed into a fixed bed with 5 A molecular sieves for adsorption separation, wherein the adsorption temperature was 200° C.; the feedstock mass space velocity was 0.3 h$^{-1}$; the 5 A molecular sieve bed layer had a height to diameter ratio of 8:1; the adsorption lasted for 30 minutes. The gas not adsorbed by the 5 A molecular sieves was condensed to obtain a raffinate oil rich in naphthenes and arenes. The adsorbed material was desorbed with nitrogen gas at a desorption temperature of 400° C. and a desorbing agent feedstock space velocity of 200 h$^{-1}$, to obtain a desorbed oil rich in normal paraffins.

The resultant raffinate oil was catalytically reformed according to the process in Comparative Example 1. The results are shown in Table 3.

TABLE 3

| | Example | | | | Comparative Ex. 1 | Comparative Ex. 2 |
|---|---|---|---|---|---|---|
| | 2 | 3 | 4 | 5 | | |
| Catalyst No. | B | B | C | D | B | B |
| Reaction pressure, MPa | 0.35 | 0.35 | 1.4 | 1.4 | 0.35 | 0.35 |
| Hydrogen/hydrocarbon ratio, mol/mol | 6.7:1 | 6.7:1 | 6.7:1 | 6.7:1 | 6.7:1 | 6.7:1 |

TABLE 3-continued

|  | Example | | | | | |
|---|---|---|---|---|---|---|
|  | 2 | 3 | 4 | 5 | Comparative Ex. 1 | Comparative Ex. 2 |
| Catalyst No. | B | B | C | D | B | B |
| Reaction temperature, °C. | 500 | 500 | 475 | 475 | 500 | 500 |
| Volume space velocity of the feedstock, h$^{-1}$ | 20 | 8 | 20 | 18 | 2 | 2 |
| C$_5^+$ reformate yield, mass % | 98.35 | 96.23 | 95.88 | 94.01 | 89.72 | 91.46 |
| Arene content, mass % | 34.83 | 50.82 | 32.62 | 31.89 | 78.50 | 80.56 |
| Naphthene conversion ratio, mass % | 92.01 | 97.30 | 91.92 | 92.20 | 99.33 | 99.16 |
| Conversion ratio of paraffins to arenes and C$_4^-$-olefins, mass % | 5.74 | 27.83 | 7.23 | 7.92 | 70.43 | 72.82 |

Examples 6-8

In a 100 ml fixed-bed continuous flow reactor, 50 ml of PtRe/γ-Al$_2$O$_3$ catalyst B and the refined naphtha listed in Table 2 as the catalytically reforming feedstock were used to study the effects of different reaction temperatures and feedstock volume space velocities on the catalytically reforming reaction at a reaction pressure of 0.70 MPa and a hydrogen/hydrocarbon molar ratio of 2.2:1. The reaction feedstock inlet temperatures, feedstock volume space velocities and reaction results in the examples are shown in Table 4.

Example 9

In a 100 ml fixed-bed continuous flow reactor, 50 ml of PtRe/γ-Al$_2$O$_3$ catalyst C was fed and the refined naphtha listed in Table 2 as the catalytically reforming feedstock was reformed according to the process disclosed herein under the conditions of a reaction pressure of 1.30 MPa, a hydrogen/hydrocarbon molar ratio of 4.5:1, a reaction temperature of 436° C., a feedstock volume space velocity of 2.1 h$^{-1}$. The reaction results are shown in Table 4.

TABLE 4

|  | Example | | | |
|---|---|---|---|---|
|  | 6 | 7 | 8 | 9 |
| Catalyst No. | B | B | B | C |
| Reaction pressure, MPa | 0.7 | 0.7 | 0.7 | 1.3 |
| Hydrogen/hydrocarbon ratio, mol/mol | 2.2:1 | 2.2:1 | 2.2:1 | 4.5:1 |
| Reaction temperature, °C. | 389 | 427 | 489 | 436 |
| Volume space velocity, h$^{-1}$ | 2.1 | 2.1 | 11.9 | 2.1 |
| Yield of C$_5^+$ reformate, mass % | 98.83 | 98.09 | 95.91 | 96.02 |
| Arene content, % | 32.68 | 35.84 | 35.82 | 32.80 |
| Naphthene conversion ratio, mass % | 87.66 | 92.89 | 87.23 | 92.21 |
| Conversion ratio of paraffins to arenes and C$_4^-$olefins, mass % | 0.83 | 5.96 | 10.74 | 7.08 |

According to Tables 3 and 4, it can be seen that, when keeping the conversion of naphthenes to arenes, by decreasing the reaction temperature or increasing the volume space velocity of the feedstock, the conversion ratio of paraffins to arenes and C$_4^-$ hydrocarbons was greatly reduced in the process disclosed herein, and most of the paraffins were remained as compared with the conventional reforming reaction. In the process disclosed herein, the naphthene conversion ratio reached, for example, more than 85 mass %, and the conversion ratio of paraffins to arenes and C$_4^-$ olefins was, for example, less than 30 mass %. In most cases, the conversion ratio of paraffins to arenes and C$_4^-$ olefins was less than 10 mass %.

Example 10

The following examples show the effect of the C$_5^+$ reformate obtained by the process disclosed herein after separation of arenes.

By using sulfolane as the solvent for extraction separation of arenes, the C$_5^+$ reformate obtained in Example 2 was contacted with sulfolane in the extraction tower, wherein the solvent/feedstock mass ratio was 2:1; the extraction tower top pressure was 0.45 MPa; the reflux ratio was 0.25; the temperature at which the solvent was fed into the tower was 85° C.; and the temperature at which the feedstock was fed into the tower was 50° C.

A solvent rich in arene compounds was obtained at the bottom of the extraction tower; a raffinate liquid containing non-arene compounds was obtained at the top of the tower. The solvent rich in arene compounds was distilled and separated from the extraction solvent to obtain mixed arenes, and the raffinate liquid was water-washed to remove the residual trace solvent to obtain a hydrocarbon mixture rich in paraffins. The yields of the hydrocarbon mixture rich in paraffins (relative to naphtha) and arenes (relative to arenes in the C$_5^+$ reformate) are shown in Table 5.

Example 11

The C$_5^+$ reformate obtained in Example 3 was treated in the same way as Example 10. The yields of the hydrocarbon mixture rich in paraffins (relative to naphtha) and arenes (relative to arenes in the C$_5^+$ reformate) are shown in Table 5.

Comparative Example 3

This comparative example shows the effect of the conventional catalytic reformed C$_5^+$ oil after separation of arenes.

According to the process in Example 10, arenes and paraffins in the C$_5^+$ reformate obtained in Comparative Example 1 were separated by using sulfolane as the extraction solvent. The yields of the hydrocarbon mixture rich in paraffins (relative to naphtha) and arenes (relative to arenes in the C$_5^+$ reformate) are shown in Table 5.

Comparative Example 4

The naphtha listed in Table 1 was fed into a fixed bed with 5 A molecular sieves for adsorption separation, wherein the adsorption temperature was 200° C.; the feedstock mass space velocity was 0.3 h$^{-1}$; the 5 A molecular sieve bed layer had a height to diameter ratio of 8:1; and the adsorption lasted for 30 minutes. The gas not adsorbed by the 5 A molecular sieves was condensed to obtain a raffinate oil rich in naphthenes and arenes. The adsorbed material was desorbed with nitrogen gas at a desorption temperature of 400° C. and a desorbing agent feedstock space velocity of 200 h$^{-1}$, to obtain a desorbed oil rich in normal paraffins. The yield thereof relative to naphtha is shown in Table 5.

TABLE 5

|  | Example 10 | Example 11 | Comparative Example 3 | Comparative Example 4 |
|---|---|---|---|---|
| Arene yield, mass % | 95 | 98 | 98.5 |  |
| Yield of hydrocarbon mixture rich in paraffins, mass % | 65.81 | 48.31 | 20.35 | 29.60 |

The results in Table 5 show that the yield of the hydrocarbon mixture rich in paraffin obtained by the process disclosed herein is greatly increased as compared with those obtained by the conventional reforming and adsorption-separation processes. The process disclosed herein can achieve more paraffins, which are good feedstocks for production of ethylene by cracking. This shows that the process disclosed herein may sufficiently utilize the ingredients in naphtha and maximally obtain paraffins while producing arenes, so as to make naphtha become the feedstock for both producing arenes and maximally obtaining ethylene cracking materials of good quality.

Example 12

This example shows the steam cracking effect of the hydrocarbon mixture rich in paraffins obtained by the process disclosed herein.

The hydrocarbon mixture rich in paraffins obtained according to Example 10 was used as the steam cracking material. The steam cracking reaction was carried out under the conditions of a cracking furnace outlet pressure 0.185 MPa, a residence time of 0.20 s, a water/oil mass ratio of 0.55:1, and a cracking furnace outlet temperature of 840° C. The ethylene yield is shown in Table 6.

Example 13

The hydrocarbon mixture rich in paraffins obtained according to Example 11 was used as the steam cracking material. The steam cracking reaction was carried out under the conditions of a cracking furnace outlet pressure 0.185 MPa, a residence time of 0.20 s, a water/oil mass ratio of 0.55:1, and a cracking furnace outlet temperature of 840° C. The ethylene yield is shown in Table 6.

Comparative Example 5

This example shows the steam cracking effect of the hydrocarbon mixture rich in paraffins obtained by conventional catalytically reforming and arene-extraction processes.

The hydrocarbon mixture rich in paraffins obtained by extraction-separation of arenes in Comparative Example 3 was used as the feedstock for steam cracking, and cracked according to the process in Example 12. The ethylene yield is shown in Table 6.

Comparative Example 6

This example shows the steam cracking effect of the hydrocarbon mixture rich in normal paraffins obtained by an adsorption-separation process from naphtha.

The desorbed oil rich in normal paraffins obtained by the adsorption-separation process in Comparative Example 4 was used as the feedstock for steam cracking, and cracked according to the process in Example 12. The ethylene yield is shown in Table 6.

TABLE 6

|  | Example 12 | Example 13 | Comparative Example 5 | Comparative Example 6 |
|---|---|---|---|---|
| Cracking materials | Reformed Raffinate oil of the present disclosure | Reformed Raffinate oil of the present disclosure | Conventionally Reformed Raffinate oil | Adsorption-separated n-alkanes |
| Ethylene yield (relative to the steam cracking feedstock), mass % | 34.42 | 32.74 | 29.68 | 38.12 |
| Yield of three olefins* (relative to the steam cracking feedstock), mass % | 54.91 | 53.29 | 50.41 | 57.95 |
| Ethylene output/100 Kg naphtha, Kg | 22.65 | 14.83 | 6.05 | 11.28 |
| Output of three olefins*/100 Kg naphtha, Kg | 36.14 | 24.14 | 10.27 | 17.15 |

*Three olefins refer to ethylene, propylene, and 1,3-butadiene.

The results in Table 6 show that after naphtha was adsorption-separated, the normal paraffins obtained by the adsorption-separation had a low yield although the yields of steam-cracked ethylene and three olefins from the hydrocarbon mixture rich in normal paraffins was higher. Thus, the production of feedstocks useful for steam cracking were correspondingly and greatly decreased, wherein the output of ethylene and three olefins relative to 100 kg naphtha was respectively 11.28 kg and 17.15 kg, which are lower than those in Examples 12 and 13. As compared with the conventional catalytic reforming, the process disclosed herein achieves an increase of the output of ethylene and three olefins per 100 kg naphtha.

Example 14

This example shows the ethylene and arene yields obtained from 100 kg naphtha by the process disclosed herein.

The refined naphtha in Table 2 was catalytically reformed according to the process in Example 2 to obtain a $C_5^+$ reformate. Arenes were extracted and separated from the reformate according to the process in Example 10. Then, the resultant hydrocarbon mixture rich in paraffins was steam-cracked according to the process in Example 12. The ethylene and arene outputs are shown in Table 7.

Comparative Example 7

Present comparative example shows the ethylene and arene outputs obtained from 100 kg naphtha according to a conventional method.

100 kg naphtha were divided into two parts, wherein one was in an amount of 62.90 kg, and the other was in an amount of 37.10 kg.

62.90 kg naphtha was adsorption-separated according to the process in Comparative Example 4. The desorbed oil rich in normal paraffins obtained after separation was steam-cracked under the cracking conditions according to Example 12, and the raffinate oil was catalytically reformed according to the process in Comparative Example 1. Then 37.10 kg naphtha was steam-cracked under the cracking conditions according to Example 12. The outputs of ethylene and arenes obtained by the two processes are shown in Table 7.

TABLE 7

|  | Example 14 | Comparative Example 7 |
|---|---|---|
| Naphtha, kg | 100 | 100 |
| Ethylene output, kg | 22.65 | 18.12 |
| Output of three olefins, kg | 36.14 | 29.29 |
| Arene output, kg | 32.54 | 32.50 |
| BTX output, kg | 22.12 | 21.24 |

The results in Table 7 show that, when the same arene output was obtained from 100 kg naphtha in the process disclosed herein and in the process of Comparative Example 7, the BTX output in the process disclosed herein increased by 0.88 kg, i.e. by 4.14%, the ethylene output in the process disclosed herein increased by 4.53 kg, i.e. by 25.00%, and the output of three olefins in the process disclosed herein increased by 6.85 kg, i.e. by 23.39%.

What is claimed is:

1. A process for catalytically reforming naphtha, comprising, in the presence of hydrogen gas, contacting naphtha with at least one reforming catalyst under the conditions of a pressure ranging from 0.15 to 3.0 MPa, a temperature ranging from 300 to 540° C. and a naphtha volume space velocity ranging from 8.0 to 25.0 $h^{-1}$ to carry out a shallow catalytic reforming reaction, wherein naphthene in naphtha is converted to arenes, so as to achieve a naphthene conversion ratio of greater than 85 mass %, and a conversion ratio of paraffins to arenes and $C_4^-$ hydrocarbons of less than 30 mass %, the naphtha is a straight run naphtha and comprises from 30 to 85 mass % of alkanes, from 10 to 50 mass % of naphthenes and from 5 to 30 mass % of arenes, and said reforming catalyst comprises from 0.01 to 5.0 mass % of a Group VIII metal, from 0.01 to 5.0 mass % of a halogen and from 90.0 to 99.97 mass % of an alumina support.

2. The process according to claim 1, wherein the naphthene conversion ratio is greater than 90 mass %, and the conversion ratio of paraffins to arenes and $C_4^-$ hydrocarbons is less than 10 mass %.

3. The process according to claim 1, wherein the pressure ranges from 0.2 to 2.0 MPa, and the temperature ranges from 350 to 520° C.

4. The process according to claim 1, wherein the hydrogen/hydrocarbon molar ratio in the reforming reaction ranges from 0.1:1 to 20:1.

5. The process according to claim 4, wherein the hydrogen/hydrocarbon molar ratio in the reforming reaction ranges from 1:1 to 8:1.

6. The process according to claim 3, wherein the temperature ranges from 400 to 500° C.

7. The process according to claim 1, further comprising feeding the reforming reaction product into a gas-liquid separation device to separate hydrogen gas, a liquefied gas, and a reformate.

8. The process according to claim 7, further comprising separating arenes and paraffins in the reformate by an arene separation device to obtain a fraction rich in arenes and a fraction rich in paraffins.

9. The process according to claim 8, wherein the arene separation device is chosen from an arene extraction device and an arene adsorption-separation device.

10. The process according to claim 7, wherein the reformate is a hydrocarbon mixture of $C_5^+$ or $C_6^+$ hydrocarbons.

11. The process according to claim 9, wherein at least one extraction solvent is used in the arene extraction device and is chosen from sulfolane, dimethyl sulfoxide, dimethyl formamide, N-methylpyrrolidone, N-formylmorpholine, triglycol, tetraglycol, pentaglycol, methanol and acetonitrile.

12. The process according to claim 9, wherein at least one extraction solvent and extraction feedstock are used in the arene extraction device, and the extraction solvent and the extraction feedstock used in the arene extraction device have a mass ratio ranging from 1:1 to 5:1.

13. The process according to claim 9, wherein at least one adsorbent is used in the arene adsorption-separation device and is chosen from NaX and NaY.

14. The process according to claim 8, further comprising feeding the fraction rich in paraffins into a steam cracking device to carry out a cracking reaction to produce ethylene.

15. The process according to claim 14, wherein the cracking reaction is carried out under the conditions of a pressure ranging from 0.05 to 0.30 MPa, a reactant residence time ranging from 0.01 to 0.6 s, a water/oil mass ratio ranging from 0.3:1 to 1.0:1, and a cracking furnace outlet temperature ranging from 760 to 900° C.

16. The process according to claim 1, wherein the naphtha is a hydrocarbon mixture having an ASTM D-86 initial boiling point ranging from 40 to 80° C. and a final boiling point ranging from 160 to 220° C.

17. The process according to claim 1, wherein the straight run naphtha is a hydrorefined straight run naphtha comprising sulfur in an amount of less than 0.5 µg/g, nitrogen in an amount of less than 0.5 µg/g, arsenic in an amount of 1.0 ng/g, and lead in an amount of less than 10 ng/g.

* * * * *